United States Patent [19]

Delaney et al.

[11] 3,935,305

[45] Jan. 27, 1976

[54] TOOTHPASTE

[75] Inventors: Thomas James Delaney, Piscataway; William Grant Pierson, Flanders, both of N.J.

[73] Assignee: Colgate-Palmolive Company, New York, N.Y.

[22] Filed: May 30, 1974

[21] Appl. No.: 474,551

Related U.S. Application Data

[63] Continuation-in-part of Ser. Nos. 465,461, April 30, 1974, and Ser. No. 465,476, April 30, 1974, and Ser. No. 465,463, April 30, 1974, which is a continuation-in-part of Ser. No. 419,741, Nov. 28, 1973, which is a continuation-in-part of Ser. No. 389,827, Aug. 20, 1973, abandoned, and Ser. No. 295,094, Oct. 4, 1972, abandoned, said Ser. No. 465,461, is a continuation of Ser. No. 295,068, Oct. 4, 1972, abandoned, said Ser. No. 468,476, is a continuation-in-part of Ser. No. 382,827, , which is a continuation-in-part of Ser. No. 295,094.

[52] U.S. Cl. .................................................. 424/49
[51] Int. Cl.² ............................................. H61K 7/18
[58] Field of Search ................................. 424/49–58

[56] References Cited
UNITED STATES PATENTS

| 1,082,681 | 12/1913 | Danner | 424/49 |
| 1,112,180 | 9/1914 | Westenfelter | 424/49 |
| 1,716,035 | 6/1929 | Donchi | 424/49 |
| 2,024,146 | 12/1935 | Crowther | 424/49 |
| 2,128,917 | 9/1938 | Crocker | 424/49 |
| 3,590,120 | 6/1971 | Muhler | 424/49 |

FOREIGN PATENTS OR APPLICATIONS

| 1,124,756 | 10/1956 | France | 424/49 |

*Primary Examiner*—Shep K. Rose
*Attorney, Agent, or Firm*—Steven J. Baron; Murray M. Grill; Herbert S. Sylvester

[57] ABSTRACT

Toothpaste containing calcium carbonate as the principal abrasive and a lesser amount of sodium bicarbonate as an additional abrasive. The principal abrasive of the toothpaste may also be comprised of a mixture of abrasives such as chalk, silica, alumina, zirconium silicate or sodium aluminosilicate in combination with the minor amount of sodium bicarbonate. The latter may be included in amounts up to about 25%, while the former may be included in amounts up to about 60%.

16 Claims, No Drawings

TOOTHPASTE

This application is a continuation-in-part of copending applications Ser. Nos. (a) 465,461 filed on April 30, 1974 which in turn is a continuation in part of Ser. No. 295,068 filed on Oct. 4, 1972; now abandoned (b) 465,476, filed on April 30, 1974 which is in turn a continuation in part of copending application Ser. No. 389,827, filed on Aug. 20, 1973, now abandoned which was in turn a continuation in part of copending application Ser. No. 295,094, filed October 4, 1972; now abandoned and (c) 465,463, filed on April 30, 1974 which is in turn a continuation in part of application Ser. No. 419,741, filed on November 28, 1973 which was in turn a continuation in part of copending applications serial nos. 295,094 of October 4, 1972 now abandoned and 389,827 of August 20, 1973, now abandoned the entire disclosures all the benefit of which filing dates are claimed, of which are incorporated herein by reference.

This invention relates to toothpastes and more particularly to toothpastes containing as an adjunct abrasive, dispersed particles of sodium bicarbonate. The invention also relates to a dental cream composition suitable for use in an unlined aluminum tube.

Baking soda has been employed in many fields and is a common household ingredient. In past years, its use in dentifrices, particularly tooth powders, has been proposed but has not received much acceptance generally. The typical dentifrice which have had significant consumer acceptance in recent years are toothpastes having a high content of water-insoluble abrasives such as dicalcium phosphate or other insoluble phosphates in an aqueous humectant base.

The development of a practical and effective baking soda-containing toothpaste capable of consumer acceptability presents many special considerations. Among the factors which are to be considered are the unique character of baking soda chemically, physically and cosmetically when considered and employed as a toothpaste ingredient. For example, it is comparatively water-insoluble and tends to release carbon dioxide in an aqueous system. It is extremely salty to the taste which is probably one of the more important factors in the purchase and use of a particular product. Other factors in formulation of a suitable product include the over-all cleaning and polishing power of the product, its stability and appearance combined with special care in manufacture, etc.

In formulating a dentifrice based on precipitated calcium carbonate, the incompatibility of calcium carbonate with acids and most fluoride salts must be taken into account due to the character thereof. As can be seen, the problems are thus two fold where a dentifrice includes both baking soda and chalk therein. The foregoing is one from among the many difficulties which the instant invention overcomes and obviates.

A further feature of the invention is directed to the packaging of dental creams in unlined aluminum tubes, which is desired in view of the relatively low cost of such tubes and of their light weight. When dental creams are packaged in unlined aluminum containers, it is sometimes found that the containers corrode and/or dental cream formulations become unstable.

The present invention provides a dental cream composition suitable for use in, and compatible with, an aluminum container comprising a dental cream vehicle having dispersed or dissolved therein about 20% to 60% abrasive, which abrasive is principally calacium carbonate, with a minor amount of baking soda.

In that embodiment of the invention where the dental cream is packaged in unlined aluminum tubes and wherein there is additionally present alumina as an abrasive the inclusion of about 0.05 – 0.25% of dissolved or dispersed silicate is advantageous in order to render the dental cream more compatible with an unlined aluminum container. Furthermore, calcium carbonate acts to stabilize the composition with consequent retention of active fluoride. Dental cream compositions containing calcium carbonate have added effectiveness in connection with stain removal from teeth.

Calcium carbonate in the form of chalk may be used. Chalk in the form of a powder having a particle size of between 1 and 10 microns is preferred. It is also preferred to use a grade of calcium carbonate of moderate apparent specific gravity, e.g., about 0.7 to 0.9. If desired, calcium carbonate grades of higher apparent specific gravity, e.g., 1.19 to 1.29 may be used. "Apparent specific gravity" refers to the untamped specific gravity of the calcium carbonate. Calcium carbonate, particularly in the form of chalk, often contains magnesium carbonate as an impurity. Calcium carbonate containing even small quantities of magnesium carbonate, e.g. about 0.1 – 0.3%, tends to adversely affect the stability of a fluoride cream with consequent loss of active fluoride. The stable dental creams of the present invention tolerate small amounts of impurity, e.g., magnesium carbonate in amounts less than about 1%. However, it is preferred that the magnesium carbonate should be about 0.1–0.5% based on the calcium carbonate, especially when fluoride is present.

Furthermore, the presence of magnesium carbonate impurity in calcium carbonate or chalk tends to adversely affect the compatibility of the dental cream with unlined aluminum surfaces in which it may be packaged. When magnesium carbonate impurity is present in amounts of at least about 0.1% of the total calcium carbonate, it is desirable to include between about 0.025% and 0.25% of a dissolved or dispersed silicate in the dental cream in order to render it more suitable for compatible use in an unlined aluminum container.

In accordance with various aspects of this invention, it is now possible to prepare a unique baking soda toothpaste for use in aluminum tubes in accordance with several embodiments of the invention which is effective in promoting hygiene in the oral cavity and capable of consumer desirability or acceptability by the public. Such product will have acceptable cleaning, polishing and other desirable characteristics so as to have a beneficial effect upon parts of the dentition (which may include the teeth and its surrounding or adjacent elements or structures including plaque, calculus, gingiva, mucous membranes, saliva, etc.). In particular, it tends to leave with the consumer desirable clean mouth or clean mouth-feel effect. The product can be formulated so it is stable upon aging or storage without significant release of carbon dioxide bubbles or other forms of undesirable separation or reaction. It is possible to produce and maintain, at certain levels of bicarbonate, a substantially dispersed non-crystalline-appearing granulate which is due in part to the substantially homogeneous distribution of macroscopic crystalline bicarbonate particles or granules in an otherwise smooth, continuous base, or matrix, contributing to appearance, taste, effect and usage by the consumer.

One aspect of the invention relates to a toothpaste containing an abrasive content comprising a major proportion of a wate-insoluble dental abrasive material or mixtures thereof and sodium bicarbonate in the dental cream. Thus the toothpaste contains dispersed abrasive particles, the abrasive being a mixtures of, for example, calcium carbonate, which constitutes the major proportion of the abrasive by weight and preferably makes up about 20 to 60% of the toothpaste, and a lesser amount of sodium bicarbonate. The water-insoluble dental abrasive may be chalk, silica, alumina, zirconium silicate, sodium aluminosilicate, or other compatible silicate or carbonate which is non-reactive with the bicarbonate, or a mixture or two or more of such water-insoluble abrasives. Advantageously, the amount of water-insoluble abrasive is over 20% and preferably at least about 25% of the toothpaste, ordinarily about 25–50%, more preferably about 25–35%.

Although the sodium bicarbonate particles are relatively soft as compared to most conventional abrasive particles used in toothpastes they do exert a mechanical cleaning effect on the teeth. For instance, in a radioactive dentin abrasion (RDA) test a toothpaste containing about 50% of bicarbonate of soda, as the sole abrasive, may show an RDA value of about 100 whereas when the abrasive-free vehicle of that toothpaste is tested similarly the RDA value is only in the neighborhood of 50.

The toothpastes of this invention preferably contain 1% up to about 25%, more preferably about 10–20%, sodium bicarbonate. The particle size of the sodium bicarbonate particles may vary; it is preferred that they be largely below 0.40 mm in diameter, with a major proportion by weight being above 0.01 mm in diameter. The vehicle in which the sodium bicarbonate particles are dispersed is preferably aqueous, but its amount and character are preferably such that the sodium bicarbonate is primarily in the undissolved solid state in the toothpaste. It will be understood, however, that when the teeth are brushed the sodium bicarbonate particles will tend to dissolve in the saliva.

In one particularly preferred form of the invention the water-insoluble principal abrasive is chalk. It is found that this ingredient greatly improves the cleaning power of the sodium bicarbonate. In addition, the presence of the chalk appears to promote an improvement in the stability of the toothpaste on aging at elevated temperatures such as a decrease in the tendency for essential oils used as flavors, to separate from the toothpaste on aging at 110° or 120°F, e.g. when the particles of sodium bicarbonate are of relatively large size, e.g., over 150 microns in diameter.

The combination of the compatible water-soluble abrasives such as chalk, silica, alumina, zirconium silicate, and the like, or mixtures thereof is found to yield a sodium bicarbonate containing toothpaste which has improved cleaning power combined with resistance to flavor separation and which does not tend to form gas on storage. In contrast, when such common dental abrasives as dicalcium phosphate or insoluble sodium metaphosphate are added to the sodium bicarbonate toothpaste considerable quantities of gas maybe formed even on short term storage (e.g. at 120°F.), that is, when included in sufficient quantity.

The average particle size of the chalk is preferably less than 20 microns, most preferably below 10 microns and above 1 micron as earlier stated. Tables I and II below show the particle size ranges and densitites of various grades of chalk that may be employed herein.

TABLE I

Sturge Precipitated Calcium Carbonates Particle size,[a] diameter (μ)

| Grade | 0–3 | 3–6 | 6–10 | Over 10 | Apparent density (g/ml) |
|---|---|---|---|---|---|
| Light | 80% | 14% | 4% | 2% | 0.351–0.430 |
| Medium | 67 | 17 | 12 | 4 | 0.500–0.588 |
| Dense | 55 | 21 | 16 | 8 | 0.727–0.851 |
| Extra dense | 50 | 20 | 20 | 10 | 0.870–1.050 |

[a] From data obtained by microscopic count.

TABLE II

Particle Size Distribution of Precipitated Chalk (U.S.P.) Weight below indicated size (%)

| Diameter (μ) | Heavy | Medium | Light | Extra light |
|---|---|---|---|---|
| 10.0 | 85.3 | 97.7 | 98.6 | 98.8 |
| 7.5 | 66.4 | 92.9 | 96.8 | 98.8 |
| 5.0 | 30.6 | 61.4 | 85.7 | 95.6 |
| 4.0 | 14.9 | 43.7 | 77.5 | 93.1 |
| 3.0 | 7.3 | 32.1 | 52.1 | 70.6 |
| 2.0 | 3.6 | 19.7 | 20.0 | 27.7 |
| 1.0 | 2.1 | 10.1 | 10.2 | 10.5 |
| 0.5 | — | 5.1 | 5.2 | 5.5 |

One particularly suitable alumina is in the form of flat flakes of alpha-alumina crystals, of disk- or plate-like configuration, said flakes having a mean (by weight) particle diameter of less than about 7 microns (e.g. about 2 to 7 microns). The flat alpha-alumina crystals, and a process for preparing them, are described in U.S. Pat. No. 3,121,623. The dentifrice is preferably substantially free of anhydrous alumina particles having diameters above 15 microns and thicknesses above about 2 microns. While it is most preferred to use alumina flakes whose mean particle diameter is less than five microns (e.g. about 3 to 4 microns) it is within the broader scope of this invention to use alumina flakes of larger diameters but similar thickness, such as alumina flakes, described in the aforesaid U.S. Pat. No. 3,121,623 having average diameters of 9, 12 or 15 or more microns, free of particles over 40 microns in diameter (preferably free of particles over about 20 microns in diameter) and substantially free of particles having thicknesses above about 3 microns. In a preferred form of the invention the alpha-alumina flakes are uncoated and free of adhesion to particles of other materials. It is also within the broader scope of the invention to include other alpha-aluminas, or other abrasives of Mohs hardness above 6, in admixture with the alpha-alumina flakes. For instance, one may replace about one half of the alumina flakes by a pulverized alpha-alumina of irregular shape and having a mean particle size of about 3 to 4 microns (with all said irregular particles being less than about 7 microns in their largest dimension); thus, the toothpaste may contain, say, 3% of the flakes and 2% of said irregular particles.

A typical alkali or alkaline earth metal aluminosilicate is a complex having a refractive index of about 1.45, a moisture content of about 5–20% (e.g. 10%) an alumina content of up to about 10% (e.g. 8%) a silica content of at least about 70%, a sodium oxide (or other alkali metal or alkaline earth metal oxide, e.g. calcium oxide) content of up to about 10% (e.g. 7%) and a particle size of below 40 microns, preferably about 1 to 20 microns.

Examples of mixtures are blends of chalk and hydrated alumina, in, say, equal amounts, or about 25/75 or about 75/25.

The toothpaste may also contain a small amount of titanium dioxide powder, which has been found to have a marked polishing effect on the teeth when used in the sodium bicarbonate toothpaste.

The weight of titanium dioxide particles in the toothpaste is generally above about 0.1% of the weight of the toothpaste. The amount of $TiO_2$ be included in amounts up to about 6.0%, preferably about 0.2 to 0.6% of the weight of the toothpaste. The particle size of the $TiO_2$ is preferably about 0.1 to 1 micron.

The vehicle of the toothpaste is made up of suitable liquid preferably containing a thickening agent (e.g. a gelling agent). As indicated the vehicle is preferably aqueous, but it is within the broader scope of the invention to employ non-aqueous vehicles. Generally the liquid will contain a humectant or other viscous water-miscible material such as glycerol, sorbitol, polyethylene glycol, mannitol or mixtures thereof. When water is present it preferably constitutes about 5 to 35% (e.g. about 10 to 30%) of the total vehicle. Superior results (such as better taste) are obtained when the proportion of water is relatively low, e.g. about 10 to 20% of the total toothpaste, such as when the water to glycerol ratio is in the range of about 0.4:1 to 0.7:1.

Gelling agents for toothpaste vehicles are well known in the art. These are often high polymers (e.g. gums or other thickening agents) which are soluble or swellable in water or aqueous medium. Sodium carboxymethylcellulose has given excellent results. Other materials are gum tragacanth, gum arabic, gum karaya, sodium alginate,, hydroxyethyl cellulose, methyl cellulose, ethyl cellulose, carrageen and other polysaccharides, polyvinyl pyrollidones or such thickening agents as "Veegum" (a complex magnesium aluminum silicate). The amount of thickening agent used in the practice of this invention is preferably sufficient to impart to the mixture the pasty consistency, body and the non-tacky nature which is characteristic of conventional dental creams or toothpastes. As is well known, such dental creams are extrudable from ordinary collapsible toothpaste tubes to form a ribbon of substantial thickness (e.g. about ⅜ inch) which if left undisturbed, substantialy retains its original thickness over a period of say, one minute or more (and does not penetrate substantially into the bristles of a toothbrush when resting on the end of such bristles for a similar period); but which preferably offers no substantial resistance to brushing or to deformation when, for instance, one touches it lightly with a finger; and which has little tack, in that it does not tend to form a string when the finger is pulled away from the ribbon. The proportion of thickening agent is often within the range of about 0.5 to 2%, such as about 0.8 to 1.5%, of the toothpaste.

An organic surface active agent is preferably used in the compositions of the present invention to aid in the prophylactic action in the thorough dispersion of the composition throughout the oral cavity, and to improve cosmetic acceptability and detersive and foaming properties. Among these are water-soluble salts of the higher alkyl sulfates, such as sodium lauryl sulfate or other suitable alkyl sulfate having 8 to 18 carbon atoms in the alkyl group; water-soluble salts of sulfonated monoglycerides of higher fatty acids such as sodium coconut monoglyceride sulfonate or other suitable sulfonated monoglyceride of a fatty acid of 10 to 18 carbon atoms; salts of amides of higher fatty acid (e.g. 12 to 16 carbon atom acids) with lower aliphatic amino acids (e.g. taurine or sarcosine) or other amino acid of 2 to 6 carbon atoms, such as sodium-N-methyl-N-palmitoyl tauride, sodium N-lauroyl, N-myristoyl or N-palmitoyl sarcosinates; water-soluble salt of the esters of such fatty acids with isethionic acid or with glycerol monosulfate, such as the sodium salt of the monosulfated monoglyceride of hydrogenated coconut oil fatty acids; water-soluble salts of olefin sulfonates, e.g. alkene sulfonates or hydroxyalkane sulfonates or mixtures thereof having 12 to 18 carbon atoms in the carbon chain of the molecule; water-soluble soaps of higher fatty acids such as those of 12–18 carbon atoms e.g. coconut fatty acids. The cation of the salt may be, for instance, sodium (which is preferred) potassium or mono-di- or triethanolamine. Mixtures of surface active agents may be used. A particularly suitable mixture which provides a high foaming powder with little or no irritating effect comprises a higher alkyl sulfate and a higher fatty acid sarcosinate, e.g in a ratio of about 1:2 to 2:1, such as about 1:1; instead of all or part of the sarcosinate a higher fatty acid monoglyceride sulfonate may be present.

Other suitable surface-active materials include non-ionic agents such as condensates of sorbitan monostearate with approximately 60 of ethylene oxide, condensates of ethylene oxide with propylene oxide condensates of propylene glycol (available under the trademark "Pluronics") and amphoteric agents such as quaternized imidazole derivatives which are available under the trademark "Miranol" such as Miranol $C_2M$. Cationic surface-active germicides and antibacterial compounds may also be used. Such compounds include di-isobutylphenoxyethyoxyethyl dimethyl benzyl ammonium chloride, benzyl dimethyl stearyl ammonium chloride, tertiary amines, having one fatty alkyl group (of from 12 to 18 carbon atoms) and two (poly) oxyethylene groups attached to the nitrogen (typically containing a total of from about 2 to 50 ethenoxy groups per molecule) and salts thereof with acids, and compounds of the structure:

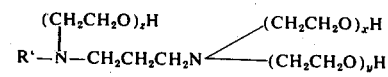

where R is a fatty alkyl group consisting from about 12 to 18 carbon atoms, and x, y and z total 3 or higher, as well as salts thereof with mineral or organic acids. It is preferred to use from about 0.05 to 5 percent by weight of the foregoing surfaceactive materials in the instant dentifrice prepartations.

The proportion of surface-active agent is preferably within the range of about 0.05 – 5% of the toothpaste, more preferably in the range of about 1 to 3%, such as about 1-½ to 2%.

In accordance with certain aspects of this invention, cationic antibacterial agents are included in the compositions of the present invention. Such agents include:
$N^1$-(4-chlorobenzyl)-$N^5$-(2,4-dichlorobenzyl) biguanide p-chlorophenyl biguanide
4-chlorobenzylhydryl biguanide;
4-chlorobenzhydrylguanylurea;

N-3-lauroxpropyl-N⁵-p-chlorobenzylbiguanide;
1-(lauryldimethylammonium)-δ-(p-chlorobenzyl-
dimethylammonium) octane dichloride;
5,6-dichloro-2-guanidinobenzimidazole;
$N^1$-p-chlorophenyl-$N^5$-laurylbiguanide;
5-amino -1,3-bis (2-ethylhexyl)-5-methylhexahy-
dropyrimidine cetyl pyridinium chloride and their non-toxic acid addition salts, particularly the fluorides and the dihydrogen fluorides. 1,6-di)p-chlorophenylbiguanidohexane) is particularly preferred. These agents may be used in amounts ranging from about 0.01 to 5 percent by weight of the dentifrice.

Any suitable flavoring or sweetening materials may be employed in formulating a flavor for the compositions of the present invention. Examples of suitable flavoring constituents include the flavoring oils, for example, oils of spearmint, peppermint, wintergreen, sassafras, clove, sage, eucalyptus, marjoram, cinnamon, lemon and orange, as well as methylsalicylate. Suitable sweetening agents include lactose, maltose, sorbitol, sodium cyclamate, perillartine, saccharine and ammoniated glycyrrhizin (e.g. its monoammonium salt). Suitably, flavor and sweetening agent together comprise from about 0.01 to 5 percent or more of the compositions of the instant invention. Preferably the amount of flavoring oil is above 0.3%, e.g. 0.8 to 1.2%.

There may also be included in like amounts, a sweetener of the neohesperidin dihydrochalcone group.

The dental cream may also contain a fluoride-containing anticaries agent. There are many water-soluble inorganic salts which are suitable sources of fluoride ions. Among these are sodium, potassium, manganese, and lithium and amine fluorides. The monofluorophosphate salts are also useful and include $Na_4P_3O_9F$, $K_4P_3O_9F$, $(NH_4)_4P_3O_9F$, $Na_3KP_3O_9F$, $(NH_4) NaP_3O_9F$, and $Li_4P_3O_9F$. Complex water-soluble fluoride-containing salts such as fluorosilicate(i.e., $Na_2SiF_6$), fluorozirconate (i.e., $Na_2ZrF_6$), fluorostannite (i.e., $KSnF_3$), fluoroborate (i.e., $NaBF_4$), fluorotitanate (i.e., $NaTiF_5$), and fluorogermanate (i.e., $K_2GeF_6$) may also be useful. The fluoride ion may also be supplied by an organic fluoride which yields fluoride ions in water. Suitable organic compounds include mono-, di-, and triethanolamine hydrofluoride. These materials are present in an effective but non-toxic amount, usually within the range to provide about 0.01 to 1 percent by weight of the water-soluble fluorine content thereof to the dentifrice. Sodium fluoride, and sodium monofluorophosphate are the preferred compounds.

Various other materials may be incorporated into the dentifrice preparations of this invention. Examples thereof are coloring and whitening agents, preservatives, silicones, chlorophyll compounds, and mixtures thereof, and other constituents. These adjuvants are incorporated in the instant compositions in amounts which do not substantially adversely affect the properties and characteristics desired and are selected and used in proper amount depending upon the particular type of preparation involved.

The following Examples are given to illustrate this invention further. In this application all proportions are by weight unless otherwise indicated.

EXAMPLE 1

A toothpaste is prepared by forming a gel by mixing a gelling agent, in this case sodium carboxymethyl cellulose ("CMC") with glycerol and water (in the presence of a sweetener, sodium saccharin, a flavor and a preservative, sodium benzoate), then adding to the gel, sodium bicarbonate (baking soda) chalk, and titanium dioxide powder and thereafter degassing the mixture under vacuum. The proportions used are: baking soda, 10%; chalk, 35%; titanium dioxide, 0.4 %; deionized water, 16.1%; glycerol, 34.0%; CMC, 1.2%, solution of 35% sodium N-lauroyl sarcosinate in a mixture of 35% water and 30% glycerol, 2%; sodium lauryl sulfate, 0.98; sodium benzoate, 0.5%; sodium saccharin, 0.2%; flavor, 0.9%.

The baking soda powder is U.S.P. grade having the following particle size distribution in which percentages represent the cumulative per cent retained on the named sieve, and sieve sizes are U.S. Standard: No. 45 sieve, trace; No. 70 sieve (sieve opening 210 microns), 27%; No. 80 sieve (sieve opening 177 microns) 66.5%; No. 100 sieve (sieve opening 149 microns), 92.5%; No. 170 sieve (sieve opening 88 microns), 99%.

The chalk is U.S.P. precipitated calcium carbonate containing at least 98% $CaCO_3$ with no more than 0.2% insoluble in dilute HCl. Its particle size is such that over 99% passes through a U.S. Standard No. 325 mesh sieve, the particles being principally in the 1 to 10 micron size, the average particle size being about 3 microns. A grit free U.S.P. non Fer Al Chalk of similar properties may also be employed with accompanying adjustment of gelling agent and viscosity.

The titanium dioxide used is a grit-free anatase powder at least 99.0% of which passes through a No. 325 U.S. Standard sieve and whose mean particle diameter (as measured on a Kahn sedimentation balance) is below 1 micron. Microscopic measurements indicate its averge particle diameter is 0.3 micron.

The toothpaste has good cleaning power and whiteness and ages well in tests at 8°F, 40°F, 110°F, 120°F. The toothpaste has a pleasant smell during brushing; while the large particles of baking soda are moderately palpable they break down to smaller particles easily under the pressure of the toothbrush and under the action of the saliva.

EXAMPLE 2

Example 1 is repeated except that the level of chalk is reduced to 25% and the level of sodium bicarbonate increased to 20%.

EXAMPLE 3

Example 1 is repeated except that 5% hydrated alumina is substituted for 5% of the chalk, the proportion of baking soda remains the same, the flavor used is a mixture of essential oils, largely peppermint.

The hydrated alumina has the following particle size distribution, and is alpha alumina trihydrate:
28–40% finer than 5 microns
56–67% finer than 10 microns
85–93% finer than 20 microns
94–99% finer than 30 microns

EXAMPLE 4

Example 3 is repeated except that instead of the 5% of hydrated alumina there is employed 5% zirconium silicate powder of the following particle size distribution:
80% finer than 1.25 microns
90% finer than 1.77 microns
95% finer than 2.15 microns
99% finer than 2.50 microns

EXAMPLE 5

Example 3 is repeated except that instead of the 5% of hydrated alumina there is used 5% of micronized silica, and half the baking soda is replaced by a more finely divided baking soda having the following particle size distribution (in which percentages represent the cumulative per cent retained on the named sieve, and sieve sizes are U.S. Standard): No. 45 sieve (sieve opening 350 microns), trace; No. 100 sieve (sieve opening 149 microns), 0.5%; No. 170 sieve (sieve opening 88 microns), 20%; No. 200 sieve (sieve opening 74 microns), 35%; No. 325 sieve (sieve opening 44 microns), 70%; No. 400 sieve, 80%.

It is also within the broader scope of the invention to use calcium pyrophosphate (e.g. the B or $\gamma$ form of calcium pyrophosphate, or mixtures of those forms in various proportions such as in about 1:1 ratio, e.g. 53% B, 47% $\gamma$), having an average particle size below about 20 microns, e.g. about 1 or 2 to 10 microns, for part of the water-insoluble abrasive in the toothpaste.

Another aspect of this invention relates to the degassing of toothpastes containing the sodium bicarbonate particles. It is found that when such toothpastes are subjected to high vacuum, e.g. above 26 inches of mercury, the paste bubbles and expands but, unlike conventional toothpastes, it does not contract to substantially its original volume on continued vacuum treatment, but instead continues to expand. It has now been found that an excellent deaerated product, having good stability and desirable rheological chracteristics can be produced by subjecting the toothpaste containing sodium bicarbonate to a vacuum of at least 26 inches of mercury so that it expands to a volume which is at least 150% (e.g. about 200%) of its volume at atmospheric pressure and then discontinuing the treatment at high vacuum when the expanded mixture begins to contract but while its volume is still at least 150% of its volume at atmospheric pressure.

EXAMPLE 6

This Example illustrates the degassing treatment of this invention. 18.3 parts of glycerol; 1.1 part of sodium carboxymethyl cellulose; 0.5 part of sodium benzoate; 0.2 part of sodium saccharin and 15.4 parts of water are mixed at 110°–115°F. for 20 minutes and placed in a vertical cylindrical container equipped with a stirrer, specifically a Dopp mixer which has a series of intermeshing counter-rotating radially disposed mixing rods located all along its height. Then 25 parts of calcium carbonate (chalk), 20 parts of sodium bicarbonate, 0.4 part of titanium doxide are added and mixed slowly while a vacuum of 27 ½ inches of mercury is applied; the speed of mixing is then increased; during this vacuum treatment, which lasts about 5 minutes, the batch rises to a volume about ⅔ greater than its volume before vacuum is applied and then decreases somewhat. The mixture is then vented to the atmosphere and 0.975 parts of sodium lauryl sulfate and 2 parts of a solution of 35% sodium lauroyl sarcosinate in a water-glycerol (35%–30%) mixture are then added, a vacuum 28.2 inches of mercury is applied and the mixture is kept under the vacuum for about 5 minutes while stirring; during this time, the volume of the batch increases and decreases somewhat, the volumes being little greater than observed during the preceding vacuum treatment. The mixture is then vented to the atmosphere. 15.1 parts of glycerol are added and the mixture is then stirred under a vacuum of 28 inches of mercury for about 5 minutes during which treatment its volume increases by more than 100% (i.e. to a volume which is more than 200% of the original volume) and then begins to decrease somewhat. At the conclusion of this 5 minutes period, the vessel is vented to the atmosphere while the volume of the mixture is still about 75–100% greater than its volume just prior to this vacuum treatment. One part of essential oil flavor is then added, stirring is resumed while a vacuum of 28 ½ inches is applied; stirring under this vacuum is continued for about 12 minutes, after which the vessel is vented to the atmosphere; during this 12 minute period, the expansion of the mixture is similar to that observed during the immediately preceding vacuum treatment. Just before the mixture is vented to the atmosphere, the expansion of the mixture is still evident.

It is preferable to discontinue the vacuum treatment, even though expansion may continue before the change in pH (i.e. the pH of the vacuum treated mixture minus the pH of the mixture without vacuum treatment) reaches one pH unit and preferably less, e.g. ½ unit; this avoids decomposition of sodium bicarbonate and production of sodium carbonate during degassing.

In accordance with a further embodiment of the invention, the toothpaste may be prepared and degassed as follows:

The gel mix is prepared by adding the formula amount of glycerine, then adding CMC to vortex of mixing liquid and without heat, mixing for 2 minutes, then adding saccharin and sodium benzoate and further mixing for one minute. Thereafter there is added the formula amount of water, sodium lauryl sulfate and flavor. Mixing is then continued for 15 minutes. Mixing is continued until ready to drop the batch. The cover of the Dopp crutcher is then closed and there is applied 28 inches vacuum and then the vacuum valve is closed. Half the gel mix is then drawn in. The mixer is then turned off, the vacuum released and there is added formula amounts of: Titanium dioxide, Sodium N-lauroyl sarcosinate, after which there is applied vacuum to 28inch, while maintaining vacuum until the level of the cream drops. There is then drawn in the other half of gel mix and it is dearated for 5 minutes at 28 inches vacuum. Mixer is turned off, vacuum released and calcium carbonate and sodium bicarbonate added; apply vacuum with mixing. Continue mixing for 15 minutes under full vacuum. With mixer at lower speed, release vacuum and discharge cream.

EXAMPLE 7

This Example illustrates the use of alpha alumina flakes in the baking soda toothpaste.

The toothpaste is made up (using, for instance, the method of Example 1) of 10% of the baking soda powder of Example 1, 30% chalk, 5% of alpha-alumina flakes, 0.4% titanium dioxide of Example 1, 33.4% glycerol, 15.4% deionized water, 1.1% CMC (Hercules 7MF), 2% of a solution of 35% sodium N-lauroyl sarcosinate in a mixture of 35% water and 30% glycerol, 1% sodium lauryl sulfate, 1% flavor (water-insoluble essential oil flavoring agent; e.g., essential oil mixture rich in peppermint oil), 0.5% sodium benzoate and 0.2% sodium saccharin.

The alpha alumina flakes have a mean (by weight) particle diameter of about 4 microns, all the particles thereof have diameters less than 10.1 microns, about 85–95% (by weight) have diameters less than 6.0 microns and about 30–35% have particle diameters less than 3.5 microns.

The characteristics of the toothpaste of this Example are like those given in Example 1 above. It has very good resistance to flavor separation.

EXAMPLE 8

Example 7 is repeated except that the toothpaste contains 0.22% sodium fluoride (the glycerine content being correspondingly decreased by 0.22%. The toothpaste shows excellent aging characteristics including very good resistance to flavor separation on aging and very good retention of fluoride content. Like the toothpaste of Example 8, it has a high polishing effect on enamel; its percent repolish is 64%.

The percent repolish is determined by a test in which sections of human dental enamel, upon which have been ground flat areas, are first polished, then dulled with chalk, and then brushed with a slurry of a dentifrice for 5000 reciprocal strokes. A "Monsanto Tooth Reflectance Instrument" is employed to measure the specular reflectance of the surface after each step described above. The dulled surface is adjusted so that it is approximately 150 units (Monsanto Instrument) lower then the polished surface. The polishing ability of the dentifrice is expressed by the following equation:

$$\text{Percent Repolish} = \frac{(SR_{500\ strokes} - SR_{dulled})}{SR_{polished} - SR_{dulled}}$$

where $SR_{polished}$, $SR_{dulled}$ and $SR_{5000}$ strokes are respectively specular reflectance values of the enamel surface after the initial polishing, after dulling with chalk, and after brushing with a dentifrice slurry.

EXAMPLE 9

Example 7 is repeated except that the toothpaste contains 0.76% sodium monofluorophosphate (the glycerine content being correspondingly decreased by 0.76%).

EXAMPLE 10

Examples 7, 8 and 9 are repeated except that the alphaalumina flakes have a mean particle diameter of 5 microns, substantially all being less than about 12 microns in diameter.

EXAMPLE 11

This Example illustrates the use of unlined aluminum toothpaste tubes with certain baking soda toothpastes.

a. A toothpaste is made up (using, for instance, the method of Example 1) of 20% of the baking soda powder (of Example 1) 25% of calcium carbonate, (of Example 1), 0.4% titanium dioxide of Example 1, 34.02% glycerol, 16.1 deionized water, 1.2% CMC (Hercules 7MF), 2% of a solution of 35% sodium N-lauroyl sarcosinate in a mixture of 35% water and 30% glycerol, about 0.9 flavor (water-insoluble essential oil flavoring agent; e.g., essential oil mixture rich in peppermint oil), 0.5% sodium benzoate, and 0.2% sodium saccharin.

b. Example 11a is repeated except that 0.5% of fumed silica (Cab-O-Sil) is included, the amount of calcium carbonate is raised to 35%, the amount of baking soda is decreased to 10%.

c. Example 11b is repeated except that the amount of sodium bicarbonate is decreased to 5% with accompanying changes in other ingredients.

d. Example 11 is repeated four times, with additional inclusion of various proportions of non-acidic dicalcium phosphate dihydrate in the formulation, i.e., in amounts of 0.04%, 0.2%, and 0.8% (based on the weight of the formulation without said phosphate); the first case 0.04%) the titanium dioxide is omitted. The dicalcium phosphate dihydrate is of dentifrice grade and has an average particle diameter of about 4 microns and its pH (measured in 20% slurry thereof in water is in the range of 9.3 to 9.9; it yields phosphate ions on contact with water.

e. Example 11a is repeated with the additional inclusion of insoluble sodium metaphosphate in the formulation in the amount of 0.8% (based on the weight of the formulation without said phosphate). The insoluble sodium metaphosphate is of dentrifrice grade having an average particle size of about 5 microns; its pH (measured in 20% slurry thereof in water) is in the range of 5.3 to 6.3; it yields phosphate ions on contact with water.

f. Example 11a is repeated except that 5% micronized silica is substituted for 5% of the calcium carbonate, a different essential oil flavor is used, the amount of flavor is 0.9% and the amount of glycerol is 33.5%.

g. Example 11a is repeated except that 3% micronized silica is substituted for 3% of the calcium carbonate, and the toothpaste contains 0.9% of an essential oil flavor.

h. Example 11a is repeated except that 5% precipitated silica is substituted for 5 % of the calcium carbonate:

i. Example 11a is repeated except that 5% anhydrous dicalcium phosphate is substituted for 5% of the calcium carbonate; the toothpaste contains 0.9% of an essential oil flavor. The anhydrous dicalcium phosphate is a fine non-acidic powder of dentifrice grade. Its pH (as measured on a 20% slurry thereof water) is 7.6–7.8; it yields phosphate ions, in low concentration, on contact with water.

j. Example 11a is repeated except that 5% zirconium silicate of Example 3 is substituted for 5% of the calcium carbonate (with minor change in proportion and type of flavor).

k. Example 11a is repeated except that 5% beta phase calcium pyrophosphate is substituted for 5% of the calcium carbonate. The calcium pyrophosphate is a fine powder of dentifrice grade. Its pH (as measured on a 20% slurry thereof in water) is 5.2–5.3.

Each of the foregoing toothpastes is placed in an individual toothpaste tube of unlined aluminum of high purity(99.7% Al or purer) and aged. On aging at 120°F. the tube filled with the 11a toothpaste tends to swell or is found to have a foamy product film in contact with the inner aluminum walls of the tube, tubes filled with the 11b, c, d, f, g, h, i, j and k toothpastes do not show such effects. The 11 preceeding toothpastes show substantially less tendency to react with the walls of the tube than the 11a toothpaste.

The fumed silica (as in Example 11b) is described in Encyclopedia of Chemical Technology Kirk-Othmer 2nd Edition, Vol. 18 at pages 62 and 67, for instance. It is within the broader scope of the invention to use the fumed silica in baking soda toothpaste from which the compatible water-insoluble abrasive (such as calcium carbonate) has been omitted, in unlined aluminum tubes. It is also within the broader scope of the invention to employ, in place of the fumed silica, very finely dispersed or dissolved silica in other forms such as alkali metal silica such as sodium silicate, e.g. hydrated sodium silicate supplied in flake form containing $Na_2O \cdot SiO_2 \cdot H_2O$ in a ratio of about 1:2-3.2:5, or sodium silicate solutions (water glass) such as those in which the $Na_2O:SiO_2$ ratio is at least about 1:2, or sodium silicate formed in situ in the dental cream, or colloidal silica or precipitated silica (see Encyclopedia of Chemical Technology Kirk-Othmer, 2nd edition Vol. 18, pages 63 and 66–67, for instance) or other silicate.

The dicalcium phosphate dihydrate of Example 11d is a commercial stabilized dentifrice grade of this material. A description of the method of preparation of dicalcium phosphate dihydrate and of its stabilization is found in U.S. Pat. of Schlaeger et al No. 3,169,096 Feb. 9, 1965, whose disclosure is incorporated herein by reference. See also "Cosmetic Science" Vol. 1 pub. 1972 (Wiley Interscience) edited by Balsam and Sagarin pages 477–479. One typical analysis of dicalcium phosphate dihydrate indicates that its content of water-soluble material is 0.18% (and its percent water-solubles expressed as $P_2O_5$ is 0.11%). A typical stabilizer content is a mixture of about 1–2% of sodium calcium pyrophosphate and a smaller amount, e.g. about 0.4%, of pyrophosphoric acid.

The insoluble sodium metaphosphate of Example 11c is a commercial dentifrice grade of this material. Its method of preparation and properties are described in the previously cited "Cosmetic Science" at pages 480–481 and "Phosphorus and Its Compounds" by Van Wazer Vol. 2 pub. 1961 (Interscience) pages 1652–1653.

The anhydrous dicalcium phosphate of Example 11i and the calcium pyrophosphate of Example 11k are commercial dentifrice grades of these materials. See the previously cited "Phosphorus and Its Compounds" page 1651 and "Cosmetic Science" pages 479–480.

EXAMPLE 12

Example 11a is repeated except that the toothpaste contains added anhydrous disodium phosphate (incorporated as a water-soluble powder) in amount of (a) 0.05% and (b) 0.01%, the amount of water in the toothpaste being adjusted accordingly to total 100%. In each case, on aging in unlined aluminum tubes (as in Example 11) the filled tubes do not swell or gas and (after 9 weeks aging at 120°F.) the inner walls of the tubes are found to be gold-colored, the wall color in the tube containing the 12b toothpaste being very light. On inspection of the inner walls of the unlined aluminum tubes containing the 10d toothpastes (again after 9 weeks at 120°F.) they are found to be dark (when the pastes contain 0.8% or 0.4% of the dicalcium phosphate dihydrate) or golden (when the tubes contain 0.04% and 0.2% of the dicalcium phosphate dihydrate); on inspection of the inner walls of the unlined aluminum tubes containing the 11k toothpaste they are found to be golden after 3 and 6 weeks aging at 120°F. and dark after 9 weeks of such aging. It is believed that the toothpastes containing the dicalcium phosphate dihydrate contain (or form, on aging) small amounts of dissolved phosphate ions (e.g. orthophosphate and/or pyrophosphate) which may act on the aluminum walls, or on the aluminum oxide layer on said walls, to form a protective layer thereon. The amount of dissolved phosphate ion present in the preferred composition is sufficient to inhibit the gas-forming reaction between the alkaline toothpaste composition and the aluminum walls of the tube but the amount of the phosphate or acidic ingredient therein is insufficient to cause a gas-forming reaction (e.g. resulting in swelling or bursting of the tube) between the ingredients of the toothpaste; the tendency for the latter reaction can, of course, be tested by placing the composition in a suitably lined aluminum tube (whose walls are thus substantially inert to the composition) and aging for several weeks (e.g. 9 weeks) at an elevated temperature (e.g. 120°F.)

Storage of the toothpastes of other types in unlined aluminum tubes is discussed in such patents as U.S. Pat. Nos. 3,662,066 and 3,678,155 and Austrian Pat. No. 267,070. As is well known to consumers of toothpastes, aluminum toothpaste tubes are squeezed and deformable to express the toothpaste from the nozzle of the tube and the main body of the tube is of relatively thin, ductile, aluminum.

EXAMPLE 13

This Example illustrates the use of olefin sulfonate surfactant in a baking soda toothpaste; these olefin surfactants are found to produce very good foaming during tooth brushing despite the fact that the medium (saliva and baking soda toothpaste) has a relatively high concentration of dissolved electrolyte.

a. The toothpaste formulation is the same as that of Example 10 except that in place of the solution of the sarcosinate there is included about 0.7% of a sodium olefin sulfonate detergent and the amount of water is increased to about 16.6%.

b. The toothpaste formulation is the same as in Example 10 except that in place of the sodium lauryl sulfate and the solution of the sarcosinate there is included about 1.7% of a sodium olefin sulfonate detergent and the amount of water is increased to about 16.5%.

The olefin sulfonate detergent used in Example 13 is a reaction product of $SO_3$ and an olefin mixture (such as may be obtained by cracking paraffin wax) containing approximately equal amounts of 15, 16, 17 and 18 carbon atom olefins and having an average chain length of about 16 ½ carbon atoms. Other olefin sulfonate surfactants may be employed in the baking soda dentifrice. The olefin sulfonate surfactants are well known in the detergent art. Generally they contain long chain alkenyl sulfonates or long chain hydroxyalkane sulfonates (with the OH being on a carbon atom which is not directly attached to the carbon atom bearing the —$SO_3$—group). More usually, the olefin sulfonate detergent comprises a mixture of these two types of compounds in varying amounts, often together with long chain disulfonates or sulfate-sulfonates. Such olefin sulfonates are described in many patents, such as U.S. Pat. Nos. 2,061,618; 3,409,637; 3,332,880; 3,420,875; 3,428,654; 3,506,580, and British Pat. No. 1.139,158, and in the article by Baumann et al in Fette-Seifen-Anstrichmittel 72 no. 4 p. 247–253 (1970). All the above-mentioned disclosures are incorporated herein by reference. As indicated in these patents and published literature, the olefin sulfonates may be made from straight chain α-olefins, internal olefins, olefins in which the unsaturation in a vinylidene side chain (e.g. dimers of alpha olefins), etc. or, more usually, mixtures of such compounds, with the α-olefin usually being the major constituent. The sulfonation is usually carried out with sulfur trioxide under low, partial pressure, e.g.

$SO_3$ highly diluted with inert gas such as air or nitrogen or $SO_3$ under vacuum. This reaction generally yields an alkenyl sulfonic acid, often together with a sultone; the resulting acidic material is generally then made alkaline and treated to open the sultone ring to form hydroxyalkane sulfonate and alkenyl sulfonate. The number of carbon atoms in the olefin is usually within the range of 10 to 25, more commonly 12 to 20, e.g. a mixture of principally C 12, C14 and C16 having an average of about 14 carbon atoms or a mixture of principally C14, C16 and C18 having an average of about 16 carbon atoms. The preferred olefin sulfonates are sodium salts but it is within the broader scope of the invention to use other water-soluble salts such as ammonium or potassium salts.

The baking soda used in the Examples is a product made by precipitation from solution (as by treating a sodium carbonate solution with carbon dioxide to precipitate the bicarbonate) followed by drying, curing with carbon dioxide gas and screening to the desired particle size (generally without substantial crushing or pulverizing).

These particles are generally monoclinic crystals or tablets or conglomerated thereof (e.g. twinned crystals) some having projecting spike-like portions of generally rhombohedral shape with many reentraut angles.

The toothpastes of the foregoing Examples are noneffervescent. Thus when diluted with water they do not actively evolve bubbles of carbon dioxide.

The toothpastes of this invention have an alkaline pH, generally in the range of about 8.5 to 10.0, usually about 9.3 to 9.9.

The dentin abrasion of the toothpastes may be determined by the procedure based on a radioactive technique described by Grabenstetter et al in the "Journal of Dental Research", Volume 37, P. 1060 (1958) as modified by the description by Stookey et al. in the "Journal of Dental Research", Volume 47, page 524 (July-August 1968).

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A dental cream containing an abrasive system comprising about 1 – 25% sodium bicarbonate in a vehicle containing sufficient liquids, said vehicle consisting essentially of about 5 to 35% water and sufficient viscous water miscible polyol humectant or mixtures thereof and a sufficient amount of gelling or thickening agent to impart to the dental cream the pasty consistency, body and the non-tacky nature which is characteristic of conventional dental creams or toothpastes, and at least about 20% of a water-insoluble dental abrasive material compatible with said bicarbonate in the dental cream, said sodium bicarbonate being primarily in the undissolved solid state, said dental cream having a granular textured appearance comprising dispersed non-crystalline appearing granulate of macroscopic crystalline bicarbonate granules in an otherwise smooth continuous matrix.

2. A dental cream as in claim 1 wherein said insoluble abrasive is selected from the group consisting of silica, alumina, silicates, and carbonates non-reactive with the bicarbonate.

3. A dental cream sa in claim 1 wherein said insoluble abrasive is included in amounts of about 20 to 50% by weight.

4. A dental cream as in claim 1 wherein said insoluble abrasive is calcium carbonate.

5. A dental cream as in claim 4 wherein said insoluble abrasive is precipitated calcium carbonate having a density of about 0.7 to 0.9 g/cc, about 99% of which will pass through a 325 mesh sieve.

6. A dental cream as in claim 1 wherein said insoluble abrasive is flat flakes of alphaaluminum.

7. A dental cream as in claim 3 wherein said polyol is glycerol, the water: glycerol ratio being in the range of about 0.4:1 to 0.7:1.

8. A dental cream as in claim 1, containing a water-soluble polymeric gelling agent and a water-insoluble essential oil flavoring agent in the range of about 0.5 to 1.5%.

9. A dental cream as in claim 1 containing sodium carboxymethylcellulose as gelling agent.

10. A dental cream as in claim 1 containing a compatible surfactant.

11. A dental cream as defined in claim 1 wherein said bicarbonate has a particle size largely principally above about 150 microns but below about 0.4 mm in diameter.

12. A dental cream as defined in claim 1 wherein a major proportion by weight of said bicarbonate has a particle size above about 0.01 mm in diameter.

13. A dental cream as defined in claim 1 additionally containing titanium dioxide included in amounts of about 0.2 to about 6.0 percent by weight of the toothpaste.

14. A dental cream as defined in claim 13 wherein said titanium dioxide is a grit-free anatase powder at least 99.0% of which passes through a No. 325 U.S. standard sieve.

15. A dental cream as defined in claim 1 further including at least about 0–5% of a suitable flavoring oil.

16. A dental cream as defined in claim 1 further including about .01 to 5% by weight of a compatible cationic antibacterial agent.

* * * * *